(12) United States Patent
Wood et al.

(10) Patent No.: US 7,105,524 B2
(45) Date of Patent: Sep. 12, 2006

(54) PESTICIDAL AND PARASITICIDAL DI-AND TRIFLUOROSUBSTITUTED ALKENE COMPOUNDS

(75) Inventors: William Wakefield Wood, Pennington, NJ (US); David Kuhn, Newtown, PA (US); Yulin Hu, North Potomac, MD (US); Berhane Tecle, Lawrenceville, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 182 days.

(21) Appl. No.: 10/488,975

(22) PCT Filed: Sep. 9, 2002

(86) PCT No.: PCT/EP02/10074

§ 371 (c)(1),
(2), (4) Date: Mar. 9, 2004

(87) PCT Pub. No.: WO03/039258

PCT Pub. Date: May 15, 2003

(65) Prior Publication Data

US 2004/0254199 A1 Dec. 16, 2004

Related U.S. Application Data

(60) Provisional application No. 60/318,345, filed on Sep. 10, 2001.

(51) Int. Cl.
*A61K 31/519* (2006.01)
*A61K 31/4365* (2006.01)
*C07D 513/04* (2006.01)

(52) U.S. Cl. .................. 514/260.1; 544/255; 546/114; 514/301

(58) Field of Classification Search ................ 546/113, 546/114; 544/263, 255; 514/260.1, 301
See application file for complete search history.

(56) References Cited

U.S. PATENT DOCUMENTS 5,451,594 A 9/1995 Fitzjohn et al.
5,451,681 A 9/1995 Bansal et al.

FOREIGN PATENT DOCUMENTS

| EP | 405 976 | 4/1995 |
|---|---|---|
| EP | 1 000946 | 5/2000 |
| GB | 2 293 380 | 3/1996 |
| WO | 95/04727 | 2/1995 |

OTHER PUBLICATIONS

Derwent Publication Ltd., London, GB An 1999-638815 XP002210638 & WO 99/52874.

*Primary Examiner*—Bernard Dentz
(74) *Attorney, Agent, or Firm*—Novak Druce & Quigg, LLP; Jason D. Voight

(57) ABSTRACT

Di- and trifluorosubstituted alkene compounds of formula I

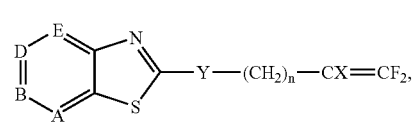

wherein
X is hydrogen or fluorine;
Y is oxygen, $NR^1$ or $S(O)_m$;
$R^1$ is hydrogen or $C_1$–$C_6$-alkyl;
m is 0, 1, or 2;
A,B,D and E are selected from the following:
a) A is N and B, D and E are $CR^2$; or
b) B is N and A, D and E are $CR^2$; or
c) D is N and A, B, and E are $CR^2$; or
d) A and D are N and B and E are $CR^2$; or
e) B and E are N and A and D are $CR^2$;
$R^2$ is H, halogen, $NH_2$, $NO_2$, CN, alkyl, haloalkyl, alkenyl, alkoxy, haloalkoxy, alkylthio, haloalkylthio, alkylsulfinyl, haloalkylsulfinyl, alkylsulfonyl, haloalkylsulfonyl, aminosulfonyl, alkoxyalkyl, alkylthioalkyl, alkylsulfinylalkyl, alkylsulfonylalkyl,alkylaminoalkyl, dialkylaminoalkyl, hydroxycarbonyl, or alkoxycarbonyl; or
phenyl which may be substituted with halogen, CN, $NO_2$, alkyl, haloalkyl, alkoxy, or haloalkoxy; or
a 5- to 6-membered heteroaromatic ring system containing 1 to 3 heteroatoms selected from oxygen, sulfur and nitrogen, which may be substituted with halogen, CN, $NO_2$, alkyl, haloalkyl, alkoxy, or haloalkoxy;
n is 1, 2, 3 or 4, and
the agriculturally and/or physiologically tolerable salts thereof,
methods for the preparation of compounds I, and compositions and methods for the control of nematodes and arachnids, and for treating, controlling, preventing and protecting warm-blooded animals, fish and humans against infestation and infection by helminths, arachnids and arthropod endo- and ectoparasites.

9 Claims, No Drawings

PESTICIDAL AND PARASITICIDAL DI-AND TRIFLUOROSUBSTITUTED ALKENE COMPOUNDS

This application is a 371 of PCT/EP02/10074 filed Sep. 09, 2002, which claims the benefit of provisional application 60/318,345 filed Sep. 09, 2001.

The present invention provides di- and trifluorosubstituted alkene compounds of formula I, $$\text{(I)}$$

[Structure: thiazolopyridine ring with substituents D, E, N, B, A, S, connected to —Y—(CH$_2$)$_n$—CX=CF$_2$]

wherein
X is hydrogen or fluorine;
Y is oxygen, NR$^1$ or S(O)$_m$;
  R$^1$ is hydrogen or C$_1$–C$_6$-alkyl;
  m is 0, 1, or 2;
A,B,D and E are selected from the following:
  a) A is N and B, D and E are CR$^2$; or
  b) B is N and A, D and E are CR$^2$; or
  c) D is N and A, B, and E are CR$^2$; or
  d) A and D are N and B and E are CR$^2$; or
  e) B and E are N and A and D are CR$^2$;
    R$^2$ is hydrogen, halogen, amino, nitro, cyano, C$_1$–C$_6$-alkyl, C$_1$–C$_6$-haloalkyl, C$_1$–C$_6$-alkenyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, C$_1$–C$_6$-alkoxy-C$_1$–C$_6$-alkyl, C$_1$–C$_6$-alkylthio-C$_1$–C$_6$-alkyl, C$_1$–C$_6$-alkylsulfinyl-C$_1$–C$_6$-alkyl, C$_1$–C$_6$-alkylsulfonyl-C$_1$–C$_6$-alkyl, C$_1$–C$_6$-alkylamino-C$_1$–C$_6$-alkyl, di-(C$_1$–C$_6$-alkyl)amino-C$_1$–C$_6$-alkyl, C$_1$–C$_6$-hydroxycarbonyl, or C$_1$–C$_6$-alkoxycarbonyl; or
    phenyl which may be substituted with any combination of 1 to 5 halogen atoms, 1 or 2 cyano groups, 1 or 2 nitro groups, 1 to 3 C$_1$–C$_4$-alkyl groups, 1 to 4 C$_1$–C$_4$-haloalkyl groups, 1 to 3 C$_1$–C$_4$-alkoxy groups or 1 to 3 C$_1$–C$_4$-haloalkoxy groups; or
    a 5- to 6-membered heteroaromatic ring system containing 1 to 3 heteroatoms selected from oxygen, sulfur and nitrogen, which may be substituted with any combination of 1 to 5 halogen atoms, 1 or 2 cyano groups, 1 or 2 nitro groups, 1 to 3 C$_1$–C$_4$-alkyl groups, 1 to 3 C$_1$–C$_4$-haloalkyl groups, 1 to 3 C$_1$–C$_4$-alkoxy groups or 1 to 3 C$_1$–C$_4$-haloalkoxy groups;
n is 1, 2, 3 or 4, and
the agriculturally and/or physiologically tolerable salts thereof.

In EP-A 405 976, anti-ulcerative thiazolopyridine compounds are described which inter alia are substituted by an optionally substituted alkene sulfide moiety.

In EP-A 1 000 946, pesticidal 2-(substituted thio)thiazolo-[4.5-b]-pyridine compounds are described which may carry a 3,4,4-trifluoro-but-3-enyl substitutent on the thio group.

However, the pesticidal and parasiticidal activity of the compounds known from the above literature in many cases is unsatisfactory.

It is, therefore, an object of the present invention to provide compounds having improved activity for the control of nematode and acarid pests and parasites and for the protection of growing and harvested crops from damage caused by nematode and acarid attack and infestation.

It is a further object of this invention to provide a method for treating, controlling, preventing and protecting warm-blooded animals, fish and humans against infestation and infection by helminths, acarids and arthropod endo- and ectoparasites.

We have found that these objects are achieved by the di- and tri-fluorosubstituted alkene compounds of formula I. Furthermore, we have found processes for preparing the compounds of formula I.

Contrary to the compounds disclosed in EP-A 405 976, in all compounds of formula I a fluorosubstituted alkene moiety is bonded to the thiazolopyridine via a heteroatom. Also, EP-A 405 976 is silent with regard to any pesticidal activity of the disclosed compounds.

The compounds of formula I differ from the compounds known from EP-A 1 000 946 in the position of the nitrogen atom in the thiazolopyridine ring.

The present invention also provides a method for the control of nematode or acarid pests which comprises contacting said pests or their food supply, habitat or breeding grounds with a pesticidally or parasiticidally effective amount of a compound of formula I.

The present invention further provides a method for the protection of growing plants from attack or infestation by nematode or acarid pests which comprises applying to the plants, or to the soil or water in which they are growing, a pesticidally effective amount of a compound of formula I.

The present invention also provides a method for treating, controlling, preventing and protecting warm-blooded animals, fish and humans against infestation and infection by helminths, arachnids or arthropod endo- and ectoparasites by use of compounds of formula I.

This invention also comprises pesticidal and parasiticidal compositions containing compounds of formula I. Compounds of formula I and compositions containing them are especially useful for the control of nematode pests.

In the definitions of the symbols given in the above formula, collective terms were used which generally represent the following substituents:
Halogen: fluorine, chlorine, bromine and iodine;
Alkyl: saturated, straight-chain or branched hydrocarbon radicals having 1 to 4 or 1 to 6 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;
Haloalkyl: straight-chain or branched alkyl groups having 1 to 4 or 1 to 6 carbon atoms (as mentioned above), where some or all of the hydrogen atoms in these groups may be replaced by halogen atoms as mentioned above, for example C$_1$–C$_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

A 5- to 6-membered heteroaromatic ring system containing 1 to 3 heteroatoms selected from oxygen, sulfur and nitrogen, e.g is pyridine, pyrimidine, pyrazine, pyridazine, triazine, triazole, pyrazole, pyrrole, imidazole, thiophene, furane, thiazole, isoxazole, or oxazole.

Alkylsulfinyl: straight-chain or branched alkyl groups having 1 to 6 carbon atoms (as mentioned above) which are attached to the skeleton via a sulfinyl group (—SO—);

Alkylsulfonyl: straight-chain or branched alkyl groups having 1 to 6 carbon atoms (as mentioned above) which are attached to the skeleton via a sulfonyl group (—SO$_2$—);

With respect to the intended use of the compounds of formula I, particular preference is given to the following meanings of the substituents, in each case on their own or in combination:

Particular preference is given to compounds of formula I wherein X is fluorine.

Preference is given to compounds of formula I wherein Y is oxygen or $S(O)_m$.

Particular preference is given to compounds of formula I wherein Y is $S(O)_m$.

Preference is given to compounds of formula I wherein m is zero or 2.

Particular preference is given to compounds of formula I wherein m is zero.

Preferred compounds of the invention are those of formula I wherein A is N and B, D and E are $CR^2$; or B is N and A, D and E are $CR^2$; or D is N and A, B, and E are $CR^2$.

Particular preference is given to compounds of formula I wherein A is N and at least two of B, D and E are CH; or B is N and at least two of A, D and E are CH; or D is N and at least two of A, B, and E are CH.

Particular preference is given to compounds of formula I wherein A is N and at least two of B, D and E are CH.

Preference is given to compounds of formula I wherein $R^2$ is hydrogen, halogen, cyano, nitro, $C_1$–$C_6$-alkyl, $C_1$–$C_6$-haloalkyl, $C_1$–$C_6$-alkoxy, $C_1$–$C_6$-haloalkoxy, or $C_1$–$C_6$-alkoxycarbonyl.

Preference is given to compounds of formula I wherein n is 2 or 4.

Particular preference is given to compounds of formula I wherein n is 2.

Formula I compounds which are especially useful for the control of nematodes include 2-(3,4,4-trifluoro-but-3-enylsulfanyl)-thiazolo[5,4-b]pyridine, 2-(3,4,4-trifluoro-but-3-enylsulfanyl)-thiazolo[5,4-c]pyridine and 2-(3,4,4-trifluoro-but-3-enylsulfanyl)-thiazolo[4,5-c]pyridine.

Particular preference is given to 2-(3,4,4-trifluoro-but-3-enylsulfanyl)-thiazolo[5,4-b]pyridine.

Particular preference is given to compounds of formula I wherein
X is hydrogen or fluorine;
Y is $S(O)_m$;
m is 0, 1 or 2;
n is 2 or 4;
A is N and B, D and E are $CR^2$; or B is N and A, D and E are $CR^2$; or D is N and A, B, and E are $CR^2$ and
$R^2$ is hydrogen, halogen, cyano, nitro, $C_1$–$C_6$-alkyl, $C_1$–$C_6$-haloalkyl, $C_1$–$C_6$-alkoxy, $C_1$–$C_6$-haloalkoxy, or $C_1$–$C_6$-alkoxycarbonyl.

Furthermore, particular preference is given to compounds of formula I wherein
X is fluorine;
Y is $S(O)_m$;
m is 0 or 2;
n is 2;
A is N and at least two of B, D and E are CH.

Likewise, particular preference is given to compounds of formula I wherein
X is fluorine;
Y is S;
n is 2;
A is N and at least two of B, D and E are CH.

Also, particular preference is given to compounds of formula I.1

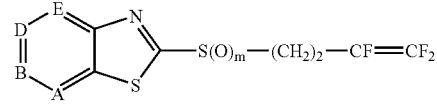

(I.1)

wherein m is 0, 1, or 2; A is N and B, D and E are CH; or B is N and A, D and E are CH; or D is N and A, B, and E are CH.

Suitable amongst agriculturally and/or physiologically tolerable salts are especially the salts of those cations which do not adversely affect the pesticidal and/or parasiticidal action of the compounds I. Thus, especially suitable cations are the ions of the alkali metals including sodium, potassium and lithium, of the alkaline earth metals including calcium and magnesium, and of the transition metals including manganese, copper, iron, zinc, cobalt, lead, silver, nickel, and also ammonium or organic ammonium including monoalkylammonium, dialkylammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$–$C_6$-cycloalkylammonium, piperidinium, morpholinium, pyrrolidinium, or benzylammonium, moreover phosphonium ions, sulfonium ions, preferably tri($C_1$–$C_4$-alkyl)sulfonium and sulfoxonium ions, preferably tri($C_1$–$C_4$-alkyl)sulfoxonium.

With respect to their use, particular preference is given to the compounds I.2 compiled in the Tables below. Moreover, the groups mentioned for a substituent in the Tables are on their own, independently of the combination in which they are mentioned, a particularly preferred embodiment of the substituent in question.

Table 1

Compounds of the formula I.2 wherein $R^2$ is hydrogen, p is 1 and the combination of X, A, B and D and the position of $R^2$ for a compound corresponds in each case to a row of Table A.

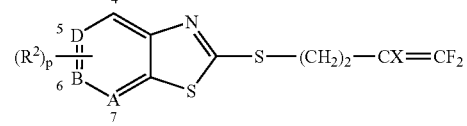

(I.2)

Table 2

Compounds of the formula I.2 wherein $R^2$ is methyl, p is 1 and the combination of X, A, B and D and the position of $R^2$ for a compound corresponds in each case to a row of Table A.

Table 3
Compounds of the formula I.2 wherein $R^2$ is ethyl, p is 1 and the combination of X, A, B and D and the position of $R^2$ for a compound corresponds in each case to a row of Table A.

Table 4
Compounds of the formula I.2 wherein $R^2$ is n-propyl, p is 1 and the combination of X, A, B and D and the position of $R^2$ for a compound corresponds in each case to a row of Table A.

Table 5
Compounds of the formula I.2 wherein $R^2$ is iso-propyl, p is 1 and the combination of X, A, B and D and the position of $R^2$ for a compound corresponds in each case to a row of Table A.

Table 6
Compounds of the formula I.2 wherein $R^2$ is n-butyl, p is 1 and the combination of X, A, B and D and the position of $R^2$ for a compound corresponds in each case to a row of Table A.

Table 7
Compounds of the formula I.2 wherein $R^2$ is iso-butyl, p is 1 and the combination of X, A, B and D and the position of $R^2$ for a compound corresponds in each case to a row of Table A.

Table 8
Compounds of the formula I.2 wherein $R^2$ is tert-butyl, p is 1 and the combination of X, A, B and D and the position of $R^2$ for a compound corresponds in each case to a row of Table A.

Table 9
Compounds of the formula I.2 wherein $R^2$ is fluorine, p is 1 and the combination of X, A, B and D and the position of $R^2$ for a compound corresponds in each case to a row of Table A.

Table 10
Compounds of the formula I.2 wherein $R^2$ is chlorine, p is 1 and the combination of X, A, B and D and the position of $R^2$ for a compound corresponds in each case to a row of Table A.

Table 11
Compounds of the formula I.2 wherein $R^2$ is bromine, p is 1 and the combination of X, A, B and D and the position of $R^2$ for a compound corresponds in each case to a row of Table A.

Table 12
Compounds of the formula I.2 wherein $R^2$ is iodine, p is 1 and the combination of X, A, B and D and the position of $R^2$ for a compound corresponds in each case to a row of Table A.

Table 13
Compounds of the formula I.2 wherein $R^2$ is cyano, p is 1 and the combination of X, A, B and D and the position of $R^2$ for a compound corresponds in each case to a row of Table A.

Table 14
Compounds of the formula I.2 wherein $R^2$ is nitro, p is 1 and the combination of X, A, B and D and the position of $R^2$ for a compound corresponds in each case to a row of Table A.

Table 15
Compounds of the formula I.2 wherein $R^2$ is methoxy, p is 1 and the combination of X, A, B and D and the position of $R^2$ for a compound corresponds in each case to a row of Table A.

Table 16
Compounds of the formula I.2 wherein $R^2$ is ethoxy, p is 1 and the combination of X, A, B and D and the position of $R^2$ for a compound corresponds in each case to a row of Table A.

Table 17
Compounds of the formula I.2 wherein $R^2$ is methoxycarbonyl, p is 1 and the combination of X, A, B and D and the position of $R^2$ for a compound corresponds in each case to a row of Table A.

Table 18
Compounds of the formula I.2 wherein $R^2$ is trifluoromethyl, p is 1 and the combination of X, A, B and D and the position of $R^2$ for a compound corresponds in each case to a row of Table A.

Table 19
Compounds of the formula I.2 wherein $R^2$ is trifluoromethoxy, p is 1 and the combination of X, A, B and D and the position of $R^2$ for a compound corresponds in each case to a row of Table A.

TABLE A

| Nr. | X | A | B | D | Position of $R^2$ |
|---|---|---|---|---|---|
| A-1 | H | N | CH | CH | 4 |
| A-2 | H | N | CH | $CR^2$ | 5 |
| A-3 | H | N | $CR^2$ | CH | 6 |
| A-4 | F | N | CH | CH | 4 |
| A-5 | F | N | CH | $CR^2$ | 5 |
| A-6 | F | N | $CR^2$ | CH | 6 |
| A-7 | H | CH | N | CH | 4 |
| A-8 | H | CH | N | $CR^2$ | 5 |
| A-9 | H | $CR^2$ | N | CH | 7 |
| A-10 | F | CH | N | CH | 4 |
| A-11 | F | CH | N | $CR^2$ | 5 |
| A-12 | F | $CR^2$ | N | CH | 7 |
| A-13 | H | CH | CH | N | 4 |
| A-14 | H | CH | $CR^2$ | N | 6 |
| A-15 | H | $CR^2$ | CH | N | 7 |
| A-16 | F | CH | CH | N | 4 |
| A-17 | F | CH | $CR^2$ | N | 6 |
| A-18 | F | $CR^2$ | CH | N | 7 |

Compounds of formula Ia

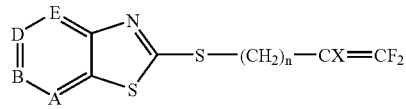

(Ia)

wherein X, A, B, D, E, and n are as defined for formula I, re obtainable by reaction of compounds of formula II

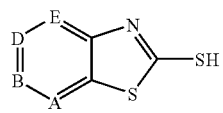

(II)

wherein A, B, D, and E are as defined for formula I, with compounds of formula III

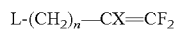   (III)

wherein X and n are as defined for formula I and L is a nucleophilic exchangeable leaving group, preferably halogen such as bromine.

The reaction is usually carried out at temperatures of from 0° C. to 150° C., preferably from 15° C. to 80° C., in an inert organic solvent in the presence of a base.

Suitable solvents are halogenated hydrocarbons, such as methylene chloride and chlorobenzene, ethers, such as dimethylether, digylme, dioxane and tetrahydrofuran, nitriles, such as acetonitrile, ketones, such as acetone, and also dimethyl sulfoxide, dimethyl formamide and dimethyl acetamide. Preferred solvents are acetone and dimethyl formamide. It is also possible to use mixtures of the solvents mentioned.

Suitable bases are inorganic compounds, such as alkali metal and alkaline earth metal carbonates, such as lithium carbonate, potassium carbonate and calcium carbonate, alkali metal bicarbonates, such as sodium bicarbonate, and also organic bases, for example tertiary amines, such as trimethyl amine, triethyl amine, tri-isopropyl ethyl amine und N-methyl-piperidine, and pyridine. Particular preference is given to alkaline earth metal carbonates, especially potassium carbonate.

In general, the base is employed in equimolar amounts or in excess.

The starting materials are generally reacted with one another in equimolar amounts. In terms of yield, it may be advantageous to use an excess of compounds of formula III based on compounds II.

Heterocyclic thiols of formula II are known or are commercially available, or they can be prepared by known methods [see e.g. Synthesis 3, 358–360 (2001)].

Compounds of formula III are known from the literature or are commercially available [see e.g. WO 86/07590 and WO 95/24403].

Sulfinyl and sulfonyl compounds of formula I wherein m is 1 or 2 may be prepared by oxidizing compounds of formula I wherein m is 0. The oxidation is usually carried out at temperatures of from (–10)° C. to 150° C., preferably from 0° C. to 60° C., in an inert organic solvent or water. Suitable oxidizing agents are, for example m-chloroperbenzoic acid, peracetic acid, $H_2O_2 \times BF_3$, $K_2S_2O_7/H_2SO_4$, peroxytrifluoroacetic acid, or hydrogen peroxide, optionally in combination with catalytic amounts of sodium tungsten dihydrate.

Suitable solvents are halogenated hydrocarbons, such as methylene chloride and chloroform alcohols, such as methanol and tert.-butanol, carboxylic acids such as acetic acid and trifluoroacetic acid, and also dimethyl sulfoxide, dimethyl formamide and dimethyl acetamide. Preferred solvents are methylene chloride and acetic acid. It is also possible to use mixtures of the solvents mentioned.

Compounds of formula I wherein X, A, B, D, E, and n are as defined for formula I and Y is OH or $NH_2$ are obtainable in a similar manner as described above for compounds of formula Ia wherein Y is S by reaction of compounds of formulae IV or V or their tautomers

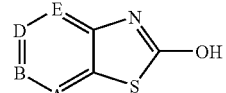   (IV)

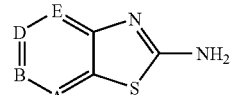   (V)

wherein A, B, D, and E are as defined for formula I, with compounds of formula III

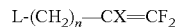   (III)

wherein X and n are as defined for formula I and L is a nucleophilic exchangeable leaving group, preferably halogen such as bromine.

The reaction is usually carried out at temperatures of from 0° C. to 150° C., preferably from 20° C. to 120° C., in an inert organic solvent in the presence of a base.

Suitable solvents are halogenated hydrocarbons, such as methylene chloride and chlorobenzene, ethers, such as dimethylether, digylme, dioxane and tetrahydrofuran, nitriles, such as acetonitrile, ketones, such as acetone, and also dimethyl sulfoxide, dimethyl formamide and dimethyl acetamide. Preferred solvents are acetone and dimethyl formamide. It is also possible to use mixtures of the solvents mentioned.

Suitable bases are inorganic compounds, such as alkali metal and alkaline earth metal carbonates, such as lithium carbonate, potassium carbonate and calcium carbonate, alkali metal bicarbonates, such as sodium bicarbonate, and also organic bases, such as tertiary amines, such as trimethyl amine, triethyl amine, tri-isopropyl ethyl amine und N-methyl-piperidine, and pyridine. Particular preference is given to alkaline earth metal carbonates, especially potassium carbonate.

In general, the base is employed in equimolar amounts or in excess.

The starting materials are generally reacted with one another in equimolar amounts. In terms of yield, it may be advantageous to use an excess of compounds of formula III based on compounds II.

Heterocyclic thiols of formula IV or V are known or can be prepared by known methods [see Heterocycles, 36, 133–144 (1993); Monatsh. Chem. 119, 333–339 (1989)].

The reaction mixtures are worked up in a customary manner, for example by mixing with water, phase separation and, if appropriate, chromatographic purification of the crude products. In some cases, the intermediates and end products are obtained in the form of colorless or pale brown viscous oils, which are purified or freed from volatile components under reduced pressure and at moderately elevated temperature. If the intermediates and end products are obtained as solids, they can also be purified by recrystallization or digestion.

If individual compounds I are not obtainable by the route described above, they can be prepared by derivatization of other compounds I.

Agriculturally and/or physiologically tolerable salts of the compounds I can be formed in a customary manner, e.g. by reaction with a base of the cation in question, preferably an alkali metal hydroxide or alkali metal hydride.

The formula I compounds of this invention are useful for the control of nematodes, especially plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula I are also useful for controlling insect and/or acarid pests, preferably acarid pests. Pests controlled by the formula I compounds of this invention include those from the order Lepidoptera, Coleoptera, Diptera, Thysanoptera, Hymenoptera, Heteroptera, Homoptera, Isoptera, Orthoptera, and Acarina.

The compounds I also are suitable for use as fungicides. They exhibit activity against a broad spectrum of phytopathogenic fungi, in particular from the classes of Ascomycetes, Deuteromycetes, Phycomycetes and Basidiomycetes. Some of them act systemically, and they can be employed in crop protection as foliar- and soil-acting fungicides.

Compounds of formula I are suitable for use as herbicides. Depending upon the application method, compounds I and herbicidal compositions comprising them may be used in crops for the control of unwanted plants. Compounds of formula I may also be used in crops that have acquired resistance against other herbicides.

The compounds of formula I are especially useful for the control of nematodes.

In practice generally about 0.1 ppm to about 10,000 ppm and preferably about 1 ppm to about 5,000 ppm of a formula I compound, dispersed in water or another liquid carrier, is effective when applied to plants or the soil or water in which the plants are growing or are to be grown to protect the plants from nematode, insect and/or acarid attack and infestation.

The di- or tri-fluorosubstituted compounds are also effective for controlling nematode, insect and/or acarid pests when applied to the pests or to their food supply, habitat or breeding ground or for protecting plants from attack or infestation by the pests when applied to the foliage, stem or roots of the plants and/or to the soil or water in which said plants are growing or are to be grown in sufficient amount to provide a rate of about 0.01 kg/ha to 100 kg/ha, preferably from about 0.1 to about 3.0 kg/ha, of active ingredient.

While the formula I compounds of this invention are effective for controlling nematode, insect and/or acarid pests of agronomic crops, both growing and harvested, when employed alone, they may also be used in combination with other biological agents used in agriculture, including other nematicides, insecticides and/or acaricides. Mixing the compounds I or the compositions comprising them in the use form as pesticides with other pesticides frequently results in a broader pesticidal spectrum of action. For example, the formula I compounds of this invention may be used effectively in conjunction or combination with pyrethroids, phosphates, carbamates, cyclodienes, formamidines, phenol tin compounds, chlorinated hydrocarbons, benzoylphenyl ureas, pyrroles and the like. The following list of pesticides together with which the compounds according to the invention can be used, is intended to illustrate the possible combinations by way of example.

Organophosphates: Acephate, Azinphos-methyl, Chlorpyrifos, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Sulprophos, Triazophos, Trichlorfon;

Carbamates: Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Bifenthrin, Cyfluthrin, Cypermethrin, Deltamethrin, Esfenvalerate, Ethofenprox, Fenpropathrin, Fenvalerate, Cyhalothrin, Lambda-Cyhalothrin, Permethrin, Silafluofen, Tau-Fluvalinate, Tefluthrin, Tralomethrin, Zeta-Cypermethrin;

Arthropod growth regulators: a) chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen;

Various: Abamectin, Acequinocyl, Amitraz, Azadirachtin, Bifenazate, Cartap, Chlorfenapyr, Chlordimeform, Cyromazine, Diafenthiuron, Dinetofuran, Diofenolan, Emamectin, Endosulfan, Endotoxin of *Bacillus thuringiensis* (Bt), Fenazaquin, Fipronil, Formetanate, Formetanate Hydrochloride, Hydramethylnon, Imidacloprid, Indoxacarb, Pyridaben, Pymetrozine, Spinosad, Sulfur, Tebufenpyrad, Thiamethoxam, and Thiocyclam.

The compounds I can be converted into the customary formulations, e.g. solutions, emulsions, microemulsions, suspensions, flowable concentrates, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

This invention also provides a method for treating, curing, controlling, preventing and protecting warm-blooded animals, including humans, and fish against infestation and infection by helminths, arachnids and arthropod endo- and ectoparasites which comprises orally, topically or parenterally administering or applying to said animals an anthelmintically, acaricidally or endo- or ectoparasiticidally effective amount of di- or tri-fluorosubstituted compound of formula I.

The above method is particularly useful for controlling and preventing helminth, nemtode, acarid and arthropod endo- and ectoparasitic infestations and infections in warm-blooded animals such as cattle, sheep, swine, camels, deer, horses, poultry, fish, rabbits, goats, mink, fox, chinchillas, dogs and cats as well as humans.

In the context of control and prevention of infestation and infections in warm-blooded animals, compounds of formula I are especially useful for the control of helminths and nematodes. Examples for helminths are members of the class Trematoda, commonly known as flukes or flatworms, especially members of the genera *Fasciola, Fascioloides, Paramphistomum, Dicrocoelium, Eurytrema, Ophisthorchis, Fasciolopsis, Echinostoma* and *Paragonimus*. Nematodes which can be controlled by the formula I compounds include the genera *Haemonchus, Ostertagia, Cooperia, Oesphagastomum, Nematodirus, Dictyocaulus, Trichuris, Dirofilaria, Ancyclostoma, Ascaria* and the like.

The formula I compounds of this invention also control endoparasitic arthropod infestations such as cattle grub and stomach bot. In addition, acarid and arthropod ectoparasitic infestations in warm-blooded animals and fish including biting lice, sucking lice, bot flies, biting flies, muscoid flies, flies, myiasitic fly larvae, gnats, mosquitoes, fleas, mites, ticks, nasal bots, keds and chiggers may be controlled, prevented or eliminated by the compounds of this invention. Biting lice include members of Mallophaga such as *Bovicola bovis, Trichodectes canis* and *Damilina ovis*. Sucking lice include members of Anoplura such as *Haematopinus eurysternus, Haematopinus suis, Linognathus vituli* and *Solenopotes capillatus*. Biting flies include members of *Haematobia*. Ticks include *Boophilus, Rhipicephalus, Ixodes, Hyalomma, Amblyomma* and *Dermacentor*. The formula I compounds may also be used to control mites which are parasitic on warm-blooded mammals and poultry including mites of the orders Acariformes and Parasitiformes.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with about 0.01 mg/kg to 100 mg/kg of animal body weight per day of the formula I compound.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with about 0.01 mg/kg to 100 mg/kg of animal body weight per day of the formula I compound.

The formula I compounds may also be applied topically to the animals in the form of dips, dusts, powders, collars, medallions, sprays and pour-on formulations. For topical application, dips and sprays usually contain about 0.5 ppm to 5,000 ppm and preferably about 1 ppm to 3,000 ppm of the formula I compound. In addition, the formula I compounds may be formulated as ear tags for animals, particularly quadrupeds such as cattle and sheep.

The formula I compounds of this invention may also be used in combination or conjunction with one or more other parasiticidal compounds including, but not limited to, anthelmintics, such as benzimidazoles, piperazine, levamisole, pyrantel, praziquantel and the like; endectocides such as avermectins, milbemycins and the like; ectoparasiticides such as arylpyrroles, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The formula I compounds may also be used in combination or conjunction with one or more compounds selected from piperonyl butoxide, N-octyl bicycloheptene dicarboximide, dipropyl pyridine-2,5-dicarboxylate and 1,5a,6,9,9a, 9b-hexahydro-4a(4H)-dibenzofurancarboxaldehyde to broaden the spectrum of activity.

The parasiticidal compositions of the present invention include a parasiticidally effective amount of a formula I compound of this invention or combinations thereof admixed with one or more agronomically acceptable and/or physiologically tolerable inert, solid or liquid carriers known from veterinary medicinal practice for oral, percutaneous and topical administration. Such compositions may comprise further additives, such as stabilizers, anifoams, viscosity regulators, binders and tackifiers. Whereas commercial products will preferably be formulated as concentrates, the end user will normally employ dilute formulations.

SYNTHESIS EXAMPLES

The compounds I obtained according to the protocols shown in the synthesis examples below together with their physical data are listed in Table I which follows.

Example 1

Preparation of 2-(3,4,4-Trifluoro-but-3-enylsulfanyl)-thiazolo[5,4-b]pyridine

A solution of thiazolo[5,4-b]pyridine-2-thiol (6.2 g) in N,N-diethyl formamide under nitrogen was treated with 1,1,2-trifluoro-4-bromobutene (8.3 g) and potassium carbonate (1.5 g), stirred at 60° C. for 24 hours, cooled, and poured into water. The resultant aqueous mixture was extracted with diethyl ether. The organic extract was dried over anhydrous sodium sulfate and concentrated in vacuo to obtain a residue. Column chromatography of the residue using silica gel and a 9:1 hexanes/ethyl acetate solution gave the title product as a colorless oil (8.9 g).

Elemental analysis: $C_{10}H_7F_3N_2S_2$

Calculated: C, 43.47; H, 2.55; N, 10.14%. Found: C, 43.46; H, 2.58; N, 10.14%.

Example 2

Preparation of 2-(3,4,4-trifluoro-4-but-3-enylsulfanyl)-thiazolo[5,4-c]pyridine

A. 2-Thio-[5,4c]thiazolopyridine

O-Ethylxanthic acid potassium salt (1.52 g) was added to a solution of 3-chloro-4-aminopyridine in N-methylpyrrolidinone (6 ml) and the mixture was heated at reflux for 4 hours, cooled to room temperature and diluted with water (30 ml). The mixture was acidified with acetic acid and filtered to give the product as a brown solid (0.68 g).

B. 2-(3,4,4-Trifluoro-4-but-3-enylsulfanyl)-thiazolo[5,4-c]pyridine

Potassium carbonate was added to a solution of the thiazolopyridine, prepared in Step A, (0.55 g) in dimethylformamide (8 ml) and the mixture was heated at 70° C. for 20 min. The mixture was cooled to room temperature and a solution of 4-bromo-1,1,2-trifluoro-1-butene on dimethylformamide (2 ml) was added. The mixture was stirred at room temperature 2 hours, diluted with water (50 ml) and extracted with ethyl acetate. The organic fraction was washed with water and saturated brine, dried over magnesium sulfate, filtered and evaporated. The residue was chromatographed on silica gel using ethyl acetate:hexanes (4:3) to give the product as a brown oil (0.55 g).

Example 3

Preparation of 2-(3,4,4-trifluoro-but-3-enylsulfanyl)-thiazolo[4,5c]pyridine

A. 2-Thio-[4,5-c]-thiazolopyridine

O-Ethylxanthic acid potassium salt (5 g) was added to 4-chloro-3-aminopyridine (2 g) in N-methylpyrrolidinone (20 ml), heated at reflux for 4 hours, cooled to room temperature and diluted with water (50 ml). The solution was acidified with acetic acid to pH and filtered to give 2.35 g of the product as a gray solid of mp. =>220° C.

B. 2-(3,4,4-Trifluoro-but-3-enylsulfanyl)-thiazolo[4,5c]pyridine

Potassium carbonate (1.9 g) was added to a solution of the thiazolopyridine (2.1 g) prepared in step 1 in dimethylformamide (30 ml). The mixture was heated at 70° C. for 25 min and cooled to room temperature. A solution of 4-bromo-1,1,2-trifluoro-1-butene in dimethylformamide (3 ml) was added and the mixture was stirred overnight at room temperature. The reaction mixture was poured into water (100 ml) and saturated aqueous sodium chloride solution (20 ml) and extracted with ethyl acetate. The organic extracts were washed with water and brine, dried over magnesium sulfate, filtered and evaporated. The residue was chromatographed on silica gel using ethyl acetate/hexanes (3/2) to give the product as a brown oil (3.16 g).

Example 4

Preparation of 2-(3,4,4-trifluoro-but-3-enylsulfinyl)-thiazolo[4,5-c]pyridine

To a solution of 2-(3,4,4-trifluoro-but-3-enylsulfanyl)-thiazolo[4,5c]pyridine (2.14 g) in methylene chloride (150 ml) there was added m-chloroperbenzoic acid (2.56 g) and the solution mixture was stirred for 30 min, after which the solvent was evaporated. The residue was dissolved in ethyl acetate (100 ml) and washed with 1% aqueous sodium chloride, dired over magnesium sulfate, filtered and evaporated. The residue was chromatographed on silica gel using hexane:ethyl acetate (7:3) to give the product as a white solid (0.8 g).

Example 5

Preparation of 2-(3,4,4-trifluoro-but-3-enylsulfonyl)-thiazolo[4,5-c]pyridine 2-(3,4,4-trifluoro-but-3-enylsulfinyl)-thiazolo[4,5-c]pyridine (0.1 g) was dissolved in methylene chloride (5 ml), m-chloroperbenzoic acid (0.07 g) was added and the mixture was stirred at room temperature for 2 hours. The mixture was washed with 1% aqueous sodium metabisulfite, aqueous sodium bicarbonate, saturated aqueous sodium chloride, dried over magnesium sulfate, filtered and evaporated. The residue was chromatographed on silica gel using methylene chloride:ethyl acetate (85:15) to give the product as a brown semi-solid (0.05 g).

TABLE I (I.1)

Structure: fused bicyclic ring with vertices labeled D, E, N, B, A, S; substituent $-S(O)_m-(CH_2)_2-CF=CF_2$

| No. | A | B | D | E | m | Physical data: $^1$H-NMR (δ [ppm]) |
|---|---|---|---|---|---|---|
| I.1-1 | N | CH | CH | CH | 0 | 2.85($m_c$), 3.55(t), 7.35($m_c$), 8.05(d), 8.45($m_c$). |
| I.1-2 | N | CH | CH | CH | 1 | 2.70($m_c$), 3.00($m_c$), 3.50($m_c$), 7.55($m_c$), 8.35(d), 8.70(d). |
| I.1-3 | N | CH | CH | CH | 2 | 3.00($m_c$), 3.75(t), 7.65($m_c$), 8.50(d), 8.80(d). |
| I.1-4 | N | OCH$_3$ | CH | CH | 0 | 2.85($m_c$), 3.55(t), 4.00(s), 6.80(d), 7.95(d). |

Examples of Action Against Animal Pests

The action of the compounds of the formula I against pests was demonstrated by the following experiments:

Activity Against Nematode Plant Diseases

Soil nematicide assay targeting root-knot nematode *Meloidogyne incognita* on tomato The test compounds were solubilized in acetone and diluted with water and surfactant to the required test concentrations. The test solution was applied as a soil drench to transplanted tomato plants in cells with sandy loam mixed with sand. One thousand root-knot J2 larvae were applied as an aqueous suspension drenched on the soil surface. The plants were maintained in the greenhouse and, one month after inoculation, the plant roots were washed free of soil. The root-knot galls on the root system of each plant were counted. Treatments were replicated three times. Percent control of root-knot was calculated for the treated plants relative to control plants treated with the acetone-surfactant carrier using the following formula:

% control of root knot galls=100×((median number of galls on control plants−median number of galls on treated plants)/median number of galls on control plants)

In this test, compound A which is known from EP-A 1 000 946 as example 1 acted as comparison active ingredient.

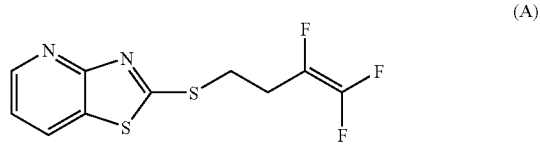

(A)

In this experiment, compound I.1—1 when applied at 0.63 kg/ha and 0.16 kg/ha, respectively, provided 100% and 94% control of root-knot while the comparison compound A provided 71% and 13% control at those same two concentrations.

Soil nematicide assay targeting root-knot nematode *Meloidogyne* sp on tomato

The test compounds were applied as granular formulations of 5% active ingredient on a gypsum carrier to soil infested with root-knot nematodes. Tomato plants were transplanted into the soil. After galling developed in untreated control plants, tomato plants were harvested and the roots assessed for root knot galling. Based on visual estimation, the percentage of the tomato root-mass that was galled was determined. Percent control root-knot was calculated for the treated plants relative to untreated control plants using the following formula:

% control of root knot galling=100×((galling level of untreated plants−galling level of treated plants)/galling level of untreated plants)

In this test, compound A which is known from EP-A 1 000 946 as example 1 acted as comparison active ingredient.

In this experiment, tomato plants that had been treated with 1 kg/ha of compound I.1—1 provided control of root knot galling of 47%, while the comparison compound A provided control of 25%.

Evaluation of Test Compounds Against *C. elegans*

Cultures of *C. elegans* (Bristol strain from J. Lewis) are maintained on *E. coli* lawns on NG Agar Plates at 20° C. Nematodes for testing are washed from cultures using Na buffer. Compounds are dissolved in 80% acetone. The test material is micropipetted (25 ml) into a single well of a 96-well sterile tissue culture plate and the solvent allowed to evaporate. A freshly prepared volume (50 ml) of *C. elegans* in Na buffer is micropipetted into each treated well and several control wells per plate. Plates are incubated at 20° C. Observations for efficacy are made under a dissecting microscope at 4 and 24 hours post-immersion. Activity is judged visually and semi-quantitatively, based on the drug effects on motility of the adults and larvae.

Activity Against Arachnids

Compounds were formulated as a 10.000 ppm solution in a mixture of 35% acetone and water, which was diluted with water, if needed.

*Tetranychus urticae* (OP-resistant Strain), 2-spotted Spider Mite (TSM)

Sieva lima bean plants with primary leaves expanded to 7–8 cm were infested by placing on each a small piece from an infested leaf (with about 100 mites) taken from the main colony. This was done at about 2 hours before treatment to allow the mites to move over to the test plant to lay eggs. The piece of leaf used to transfer the mites was removed. The newly-infested plants were dipped in the test solution and allowed to dry. After 2 days, one leaf is removed and mortality counts are made.

The invention claimed is:

1. Di- and trifluorosubstituted alkene compounds of formula I

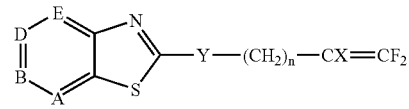

(I)

wherein
X is hydrogen or flourine;
Y is oxygen, $NR^1$ or $S(O)_m$;
$R^1$ is hydrogen or $C_1$–$C_6$-alkyl;
m is 0, 1, or 2;
A, B, D and E are selected from the following:
  A is N and B, D and E are $CR^2$; or
  A and D are N and B and E are $CR^2$; or
  B and E are N and A and D are $CR^2$;
$R^2$ is hydrogen, halogen, amino, nitro, cyano, $C_1$–$C_6$-alkyl, $C_1$–$C_6$- haloalkyl, $C_2$–$C_6$-alkenyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, $C_1$–$C_6$-alkoxy-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_1$–$C_6$-alkylamino-$C_1$–$C_6$-alkyl, di-($C_1$–$C_6$-alkyl)amino-$C_1$–$C_6$-alkyl, $C_1$–$C_6$-hydroxy-carbonyl, or $C_1$–$C_6$-alkoxycarbonyl; or
phenyl which may be substituted with any combination of 1 to 5 halogen atoms, 1 or 2 cyano groups, 1 or 2 nitro groups, 1 to 3 $C_1$–$C_4$-alkyl groups, 1 to 4 $C_1$–$C_4$-haloalkyl groups, 1 to 3 $C_1$–$C_4$-alkoxy groups or 1 to 3 $C_1$–$C_4$-haloalkoxy groups; or
a 5- to 6-membered heteroaromatic ring system containing 1 to 3 heteroatoms selected from oxygen, sulfur and nitrogen, which may be substituted with any combination of 1 to 5 halogen atoms, 1 or 2 cyano groups, 1 or 2 nitro groups, 1 to 3 $C_1$–$C_4$-alkyl groups, 1 to 3 $C_1$–$C_4$-haloalkyl groups, 1 to 3 $C_1$–$C_4$-alkoxy groups or 1 to 3 $C_1$–$C_4$-haloalkoxy groups;
n is 1, 2, 3 or 4, and
the agriculturally and/or physiologically tolerable salts thereof.

2. Compounds of formula I according to claim 1 wherein X is fluorine.

3. A process for the preparation of compounds of formula Ia

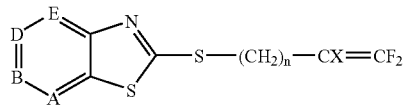

wherein X, A, B, D, E, and n are as defined in claim 1, characterized in that compounds of formula II

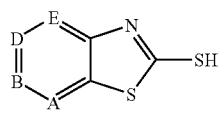

wherein A, B, D, and E are as defined for formula I in claim 1 are reacted with compounds of formula III

wherein X and a are as defined for formula I in claim 1 and L is a nucleophilic exchangeable leaving group.

4. A method for the control of nematodes or arachnids which comprises contacting said pests or their food supply, habitat or breeding ground with a pesticidally effective amount of a compound of formula I as defined in claim 1.

5. A method for the protection of plants from infestation or attack by nematodes or arachnids which comprises applying to the plants or to the soil or the water in which they are growing a pesticidally effective amount of a compound of formula I as defined in claim 1.

6. A method for treating, controlling, preventing or protecting warm-blooded animals or fish against infestation or infection by helminths, arachnids or arthrop endo- or ectoparasites which comprises orally, topically or parenterally administering or applying to said animal or fish a parasiticidally effective amount of a compound of formula I as defined in claim 1.

7. A method for the preparation of a composition for treating, controlling, preventing or protecting warm-blooded animals or fish against infestation or infection by helminths, arachnids or arthrop endo- or ectoparasites which comprises a compound of formula I as defined in claim 1.

8. A composition for the control of nematodes or arachnids which comprises an agronomically acceptable and/or physiologically tolerable carrier and a compound of formula I as defined in claim 1.

9. A composition for the control of nematodes which comprises an agronomically acceptable and/or physiologically tolerable carrier and a compound of formula I as defined in claim 1.

* * * * *

UNITED STATES PATENT AND TRADEMARK OFFICE
CERTIFICATE OF CORRECTION

| | | |
|---|---|---|
| PATENT NO. | : 7,105,524 B2 | Page 1 of 1 |
| APPLICATION NO. | : 10/488975 | |
| DATED | : September 12, 2006 | |
| INVENTOR(S) | : Wood et al. | |

It is certified that error appears in the above-identified patent and that said Letters Patent is hereby corrected as shown below:

Claim 3, column 19, indicated line 27: "X and a" should read --X and n--

Signed and Sealed this

Fifteenth Day of May, 2007

JON W. DUDAS
*Director of the United States Patent and Trademark Office*